United States Patent [19]

Tomcufcik et al.

[11] 4,344,954

[45] * Aug. 17, 1982

[54] 2,3-DISUBSTITUTED-2,3,5,6,7,8-HEXAHYDRO-THIAZOLO[3,2-A]-[1,3]DIAZEPIN-3-OLS

[75] Inventors: Andrew S. Tomcufcik, Old Tappan; William B. Wright, Jr., Woodcliff Lake, both of N.J.; Joseph W. Marsico, Jr., Pearl River, N.Y.

[73] Assignee: American Cyanamid Company, Stamford, Conn.

[ * ] Notice: The portion of the term of this patent subsequent to Aug. 11, 1998, has been disclaimed.

[21] Appl. No.: 167,088

[22] Filed: Jul. 9, 1980

[51] Int. Cl.³ .................... A61K 31/55; C07D 513/04

[52] U.S. Cl. .................... 424/270; 260/245.5;
260/239.3 R; 260/456 R; 260/456 P; 424/33;
424/34; 424/35; 424/38; 549/70; 549/72;
568/331

[58] Field of Search ...................... 260/245.5; 424/270

[56] References Cited

U.S. PATENT DOCUMENTS

| | | | |
|---|---|---|---|
| 3,763,142 | 10/1973 | Manning | 260/245.5 |
| 3,853,872 | 12/1974 | Wei et al. | 260/245.5 |
| 4,162,253 | 7/1979 | Acheson et al. | 260/245.5 |
| 4,283,334 | 8/1981 | Tomcufcik et al. | 260/245.5 |

FOREIGN PATENT DOCUMENTS 1365977  9/1974  United Kingdom ............ 260/245.5

*Primary Examiner*—Alton D. Rollins
*Attorney, Agent, or Firm*—Edward A. Conroy, Jr.

[57] ABSTRACT

This disclosure describes certain novel 2,3-disubstituted-2,3,5,6,7,8-hexahydro-thiazolo[3,2-][1,3]diazepin-3-ols which are useful as diuretic agents.

18 Claims, No Drawings

2,3-DISUBSTITUTED-2,3,5,6,7,8-HEXAHYDRO-THIAZOLO[3,2-A]-[1,3]DIAZEPIN-3-OLS

BRIEF SUMMARY OF THE INVENTION

This invention relates to new organic compounds and, more particularly, is concerned with novel 2,3-disubstituted-2,3,5,6,7,8-hexahydro-thiazolo[3,2-a][1,3]diazepin-3-ols which may be represented by the following structural formula:

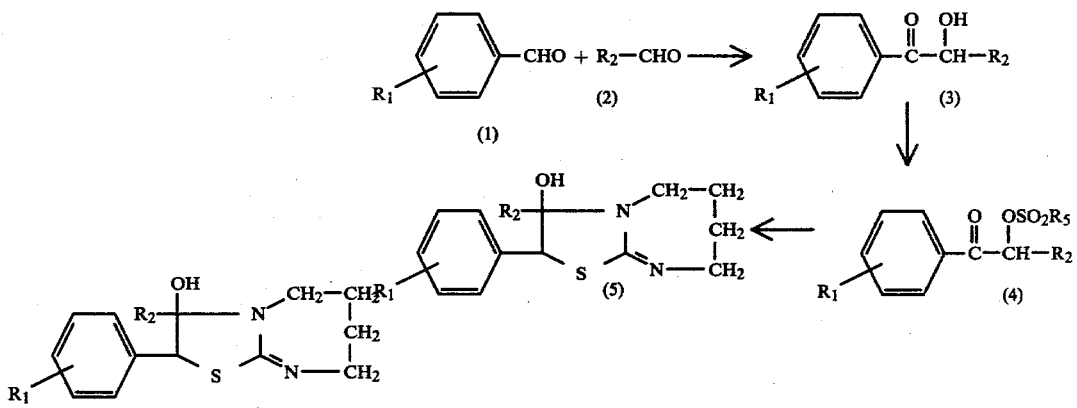

wherein $R_1$ is hydrogen, fluoro, chloro or bromo and $R_2$ is 3,4-methylenedioxyphenyl, 2-furyl, 3-methyl-2-furyl, 5-methyl-2-furyl, 2-thienyl, 3-methyl-2-thienyl, 5-methyl-2-thienyl or a moiety of the formula:

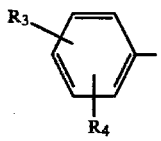

wherein $R_3$ and $R_4$ are each individually selected from the group consisting of hydrogen, fluoro, chloro, bromo, alkyl having from 1 to 3 carbon atoms, alkoxy having from 1 to 3 carbon atoms and dimethylamino. The invention also includes novel compositions of matter containing the above-defined compounds useful as diuretics and the method of enhancing the excretion of sodium ions in mammals therewith.

DETAILED DESCRIPTION OF THE INVENTION

The novel compounds of the present invention are generally obtainable as white to pale yellow crystalline materials having characteristic melting points and absorption spectra and which may be purified by recrystallization from common organic solvents such as methanol, ethanol, N,N-dimethylformamide, acetone, chloroform, ethyl acetate, and the like. They are appreciably soluble in non-polar organic solvents such as toluene, carbon tetrachloride, and the like but are relatively insoluble in water. The organic bases of this invention form non-toxic acid-addition salts with a variety of pharmacologically acceptable organic and inorganic salt-forming reagents. Thus, acid-addition salts, formed by admixture of the organic free base with one or two equivalents of an acid, suitably in a neutral solvent, are formed with such acids as sulfuric, phosphoric, hydrochloric, hydriodic, sulfamic, citric, lactic, fumaric, succinic, tartaric, acetic, benzoic, gluconic, ascorbic, and the like. The acid-addition salts are relatively insoluble in nonpolar organic solvents such as diethyl ether, benzene, toluene, and the like but are appreciably soluble in water. For purposes of this invention, the free bases are equivalent to their non-toxic acid-addition salts.

The novel compounds of the present invention may be readily prepared as set forth in the following reaction sequences:

In accordance with Reaction Sequence A, aryl aldehydes (1) and (2) undergo the benzoin condensation under the catalytic influence of an alkali metal cyanide in aqueous ethanol (50–95%) at the reflux temperature to give the acyloin (3). The acyloin (3) is then treated with an alkyl or aryl sulfonyl chloride ($R_5SO_2Cl$ wherein $R_5$ is methyl, ethyl, phenyl or tolyl) in toluene solution in the presence of triethylamine to give the ketone sulfonyl ester (4). Treatment of the ester (4) with hexahydro-2H-1,3-diazepin-2-thione in acetone solution at the reflux temperature yields the products (5) as the salts of the sulfonic acids $R_5SO_3H$.

In the process shown in Reaction Sequence A, suitable alcohols for the first step includes methanol, ethanol, isopropanol, and the like. The temperature in the first step can range from about 30° C. to about 100° C. and the time from about 30 minutes to about 4 hours. Suitable organic solvents for the second step include benzene, toluene, chloroform, and the like, tertiary amines such as trimethylamine, triethylamine, N-methylpiperidine, N-methylmorpholine, etc. The temperature in the second step can range from about 25° C. to about 80° C. and the time from about 1 to 24 hours. Suitable organic solvents for the third step include acetone, methylethylketone, chloroform, benzene toluene, and the like. The temperature in the third step can range from about 25° C. to about 60° C. and the time from about 1 to 72 hours.

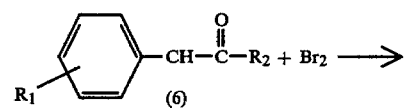

-continued
REACTION SEQUENCE B

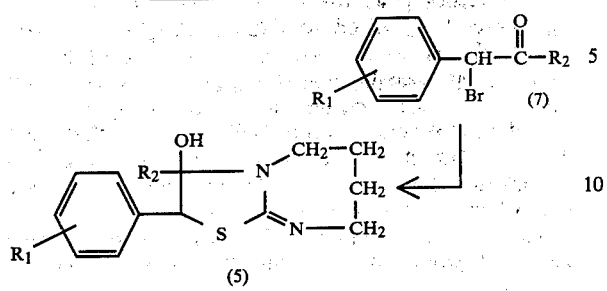

In accordance with Reaction Sequence B, a deoxybenzoil compound (6) (wherein $R_1$ and $R_2$ are as defined above) is treated with bromine in an organic solvent to yield the α-diazepin-2-thione in acetone gives the products (5).

In the process shown in Reaction Sequence B, suitable solvents in step one include acetic acid, chloroform, methylenechloride, benzene, toluene, and the like. The temperature in the first step can range from 10° C. to about 50° C. and the time from about 5 to 60 minutes. In step two, suitable organic solvents include acetone, methylethylketone, chloroform, benzene, toluene and the like. The temperature in the second step can range from about 25° C. to about 60° C. and the time from about 1 to 24 hours.

The compounds of the present invention are potent diuretics in warm-blooded animals, producing significant water diuresis and sodium ($Na^+$) loss, but with sparing loss of potassium ($K^+$), as determined in the following procedure. One to three sponteneously hypertensive rats are dosed by gavage with a test compound at 100 Mg./kg. of body weight and loaded with 0.9% sodium chloride at 25 ml./kg. of body weight at zero hour. The 0–5 hour urine is collected and $Na^+$ and $K^+$ concentrations analyzed. The results of this test on typical compounds of this invention are given in Table I, wherein the sodium and potassium levels are given in terms of milliequivalents (meq.) excreted per 5 hours with a normal sodium control being 0.60 meq. per 5 hours.

TABLE I

| Compound | Diuretic Results | | |
|---|---|---|---|
| | Urine Volume ml./5 hours | Total meq./5 Hours $Na^+$ | $K^+$ |
| 2,3,5,6,7,8-Hexahydro-2,3-diphenyl-thiazolo[3,2-a] [1,3]diazepin-3-ol hydrochloride | 20.8 | 3.13 | 0.64 |
| 2,3,5,6,7,8-Hexahydro-2,3-diphenyl-thiazolo[3,2-a] [1,3]diazepin-3-ol methanesulfonate | 15.0 | 1.42 | 0.48 |
| 2,3,5,6,7,8-Hexahydro-2,3-diphenyl-thiazolo[3,2-a] [1,3]diazepin-3-ol hydrobromide | 17.5 | 1.97 | 0.40 |
| 2-(p-Chlorophenyl)-2,3,5,6,7,8-hexahydro-3-[3,4-(methylenedioxy)-phenyl]thiazolo[3,2-a] [1,3]diazepin-3-ol | 10.0 | 1.64 | 0.45 |
| 2-(o-Chlorophenyl)-3-(p-dimethylaminophenyl)-2,3,5,6,7,8-hexahydrothiazolo[3,2-a] [1,3]diazepin-3-ol methanesulfonate | 9.2 | 1.03 | 0.54 |
| 2-(m-Bromophenyl)-3-(p-dimethylaminophenyl)-2,3,5,6,7,8-hexahydrothiazolo[3,2-a] [1,3]diazepin-3-ol methanesulfonate | 9.3 | 1.23 | 0.35 |

TABLE I-continued

| Compound | Diuretic Results | | |
|---|---|---|---|
| | Urine Volume ml./5 hours | Total meq./5 Hours $Na^+$ | $K^+$ |
| 2,3-Bis(p-chlorophenyl)-2,3,5,6,7,8-hexahydrothiazolo[3,2-a] [1,3]diazepin-3-ol hydrobromide | 6.8 | 0.85 | 0.38 |
| 2-(p-Chlorophenyl)-2,3,5,6,7,8-hexahydro-3-phenylthiazolo[3,2-a] [1,3]diazepin-3-ol hydrobromide | 13.8 | 1.78 | 0.70 |
| 2,3,5,6,7,8-Hexahydro-3-[3,4-(methylenedioxy)phenyl]-2-phenylthiazolo[3,2-a] [1,3]diazepin-3-ol methanesulfonate | 16.0 | 2.15 | 0.43 |
| 3-(2-Furyl)-2,3,5,6,7,8-hexahydro-2-phenylthiazolo[3,2-a] [1,3]diazepin-3-ol methanesulfonate | 15.3 | 1.73 | 0.45 |
| 2,3,5,6,7,8-Hexahydro-2-phenyl-3-(3,4-xylyl)thiazolo[3,2-a] [1,3]diazepin-3-ol hydrochloride | 11.0 | 1.27 | 0.49 |
| 2-(o-Chlorophenyl)-3-(3,4-dimethoxyphenyl)-2,3,5,6,7,8-hexahydrothiazolo[3,2-a] [1,3]diazepin-3-ol hydrochloride | 9.8 | 1.18 | 0.55 |
| 3-(2,4-Dimethoxyphenyl)-2,3,5,6,7,8-hexahydro-2-phenylthiazolo[3,2-a] [1,3]diazepin-3-ol hydrochloride | 10.0 | 1.14 | 0.61 |
| 2,3,5,6,7,8-Hexahydro-2,3-diphenyl-thiazolo[3,2-a] [1,3]diazepin-3-ol | 21.3 | 2.17 | 0.47 |
| 2,3,5,6,7,8-Hexahydro-2,3-diphenyl-thiazolo[3,2-a] [1,3]diazepin-3-ol tartarate | 23.0 | 2.41 | 0.41 |
| 2,3-Diphenyl-2,3,5,6,7,8-hexahydrothiazolo[3,2-a] [1,3]diazepin-3-ol salt with [4-(2-thienylcarbonyl)2,3,-dichloro]phenoxyacetic acid | 9.8 | 1.17 | 0.60 |
| 3-(p-Dimethylaminophenyl)-2-(m-fluorophenyl)-2,3,5,6,7,8-hexahydrothiazolo[3,2-a] [1,3]diazepin-3-ol methanesulfonate | 13.5 | 1.88 | 0.60 |
| 2-(m-Fluorophenyl)-3-(2-furyl-2,3,5,6,7,8-hexahydrothiazolo[3,2-a] [1,3]diazepin-3-ol methanesulfonate | 10.3 | 1.02 | 0.58 |
| 3-(p-Dimethylaminophenyl)-2-(p-fluorophenyl)-2,3,5,6,7,8-hexahydrothiazolo[3,2-a] [1,3]diazepin-3-ol methanesulfonate | 15.0 | 1.91 | 0.60 |

The compounds of the present invention have thus been shown to be valuable diuretic agents of low toxicity when administered orally. The amount of a single dose or of a daily dose will vary but should be such as to give a proportionate dosage of from about 5 mg. to about 100 mg. per day for a subject of about 70 kg. body weight. The dosage regimen may be adjusted to provide the optimum therapeutic response, for example, doses of 1.0–25 mg. may be administered on a four times per day regimen, or the dose may be proportionately increased as indicated by the exigencies of the therapeutic situation.

The compounds of the present invention may be administered as active components of compositions in unit dosage form such as tablets, pills, capsules, powders, granules, oral solutions or suspensions and the like. For preparing solid compositions such as tablets, the active compound is mixed with conventional tableting ingredients such as starch, lactose, sucrose, sorbitol, talc, stearic acid, magnesium stearate, dicalcium phosphate, gums and functionally similar materials as pharmaceutical diluents or carriers. The tablets or pills can be laminated or otherwise compounded to provide a dosage form affording the advantage of prolonged or delayed action, or predetermined successive action of the enclosed medication. For example, the tablet or pill can comprise an inner dosage and an outer dosage component, the latter being in the form of an envelop over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like. A particularly advantageous enteric coating comprises a styrene maleic acid copolymer together with known materials contributing to the enteric properties of the coating.

The liquid forms in which the compounds of the present invention may be incorporated for administration include aqueous solutions, suitably flavored syrups, aqueous or oil suspensions, flavored emulsions with edible oils such as cottonseed oil, sesame oil, coconut oil, peanut oil, and the like, as well as elixirs and similar pharmaceutical vehicles. Suitable dispersing or suspending agents for aqueous suspensions include synthetic and natural gums such as tragacanth, acacia, alginic acid, dextran, sodium carboxymethylcellulose, methylcellulose, polyvinylpyrrolidone, gelatin and the like.

The term unit dosage form refers to physically discrete units suitable as unitary dosages, each unit containing a predetermined quantity of active material calculated to produce the desired therapeutic effect in association with the required pharmaceutical diluent, carrier or vehicle. The specifications for the unit dosage forms of this invention are dictated by and are directly dependent on (a) the unique characteristic of the active material and the particular therapeutic effect to be achieved, and (b) the limitations inherent in the art of compounding such an active material for therapeutic use.

The invention will be described in greater detail in conjunction with the following specific examples.

EXAMPLE 1

2-(o-Chlorophenyl)-3-(3,4-dimethoxyphenyl)-2,3,5,6,7,8-hexahydrothiazolo[3,2-a][1,3]diazepin-3-ol A 100 g. portion of 1,4-diaminobutane in 500 ml. of 2-methoxyethanol is stirred vigorously as 86.5 g. (70 ml.) of carbon disulfide is added dropwise. The reaction is stirred for 10 minutes after the addition ends and then at reflux for one hour, clarified and cooled at 5° C. The solid is collected, washed with 100 ml. of cold isopropanol, then 200 ml. of ether and dried, giving 71 g. of hexahydro-2H-1,3-diazepin-2-thione.

A mixture of 16.6 g. of veratraldehyde, 14.0 g. of 2-chlorobenzaldehyde and 8 g. of potassium cyanide in 150 ml. of 50% ethanol is refluxed for 2½ hours, cooled, filtered and the solid is washed with water and air dried. This solid is boiled with 150 ml. of ethanol and filtered, giving 11.1 g. of 2'-chloro-3,4-dimethoxybenzoin.

A 6.13 g. portion of 2'-chloro-3,4-dimethoxybenzoin, 5.6 ml. of triethylamine and 20 ml. of toluene are mixed and stirred. A mixture of 1.55 ml. of methanesulfonyl chloride in 40 ml. of toluene is added over a period of one hour. A 50 ml. portion of water and more toluene are added. The organic layer is separated, washed with water and concentrated in vacuo to give 8.3 g. of 2'-chloro-3,4-dimethoxybenzoin methanesulfonate ester as a viscous oil. A mixture of this oil in 30 ml. of acetone is added to a stirred mixture of 1.95 g. of hexahydro-2H-1,3-diazepine-2-Thione in 150 ml. of acetone. The resulting mixture is stirred for 3 hours, then 3 hours at 45°-50° C., concentrated to ⅓ of its original volume and ether is added producing a gum. The mixture is concentrated free of solvents, 100 ml. of water and 2 ml. of ammonium hydroxide are added and the solid is filtered and washed with water. This solid is dissolved in 20 ml. of ethanol and refrigerated giving 1.3 g. of the desired product, m.p. 98°-100° C.

EXAMPLE 2

2,3,5,6,7,8-Hexahydro-3-(5-methyl-2-thienyl)-2-phenylthiazolo[3,2-a][1,3]diazepin-3-ol A mixture of 12.6 g. of 5-methyl-2-thiophenecarboxaldehyde, 5 g. of potassium cyanide and 10.1 ml. of benzaldehyde in 100 ml. of 65% ethanol is refluxed for 2 hours and then refrigerated. The solid is collected, washed with 40% ethanol then water and recrystallized twice from ethanol, giving 6.8 g. of 5-methyl-2-thienyl-α-hydroxybenzyl ketone.

A mixture of 1.71 ml. of methanesulfonyl chloride in 40 ml. of toluene is added dropwise to a stirred slurry of 4.65 g. of 5-methyl-2-thienyl-α-hydroxybenzyl ketone and 5.6 ml. of triethylamine in 40 ml. of toluene. The mixture is stirred 20 hours, water is added and the organic layer is separated, washed with water and concentrated to dryness. A 20 ml. portion of ether is added to the residue giving a solid which is collected, washed with ether and dried, giving 4.8 g. of 5-methyl-2-thienyl-α-hydroxybenzyl ketone methanesulfonate ester. A mixture of 2.01 g. of this ester and 0.84 g. of hexahydro-2H-1,3-diazepine-2-thione in 40 ml. of acetone is allowed to stand 48 hours. The solvent is removed, 50 ml. of water and one ml. of concentrated ammonium hydroxide are added and the resulting solid is collected and washed with water. This solid is dissolved in 7 ml. of ethanol and then cooled. The resulting solid is collected, washed with ethanol, then ether and dried in vacuo, giving 1.2 g. of the desired product as a yellow solid, m.p. 70°-90° C.

EXAMPLE 3

2,3,5,6,7,8-Hexahydro-2,3-diphenylthiazolo[3,2-a][1,3]-diazepin-3-ol hydrobromide A 2.6 g. portion of hexahydro-2H-1,3-diazepin-2-thione is dissolved in 150 ml. of acetone and clarified. A 5.5 g. portion of 2-bromo-2-phenylacetophenone is added and the solution is refluxed for one hour and then stirred at room temperature for 16 hours. The solid is collected, washed with acetone and dried in vacuo at 60° C., giving 6.5 g. of the desired product, m.p. 195°-197° (dec.).

EXAMPLE 4

2,3,5,6,7,8-Hexahydro-2,3-diphenylthiazolo[3,2-a][1,3]-diazepin-3-ol

A 10 g. portion of 2,3,5,6,7,8-hexahydro-2,3-diphenylthiazolo[3,2-a][1,3]diazepin-3-ol hydrobromide is dissolved with stirring in 300 ml. of 50% methanol. A 10 ml. portion of 5N sodium hydroxide is added, 200 ml. of water are added and after standing, the mixture is chilled. The solid is collected, washed with water and dried, giving 8.42 g. of the desired product, m.p. 100°–103° C.

EXAMPLE 5

2,3-Bis(p-chlorophenyl)-2,3,5,6,7,8-hexahydro-thiazolo[3,2-a][1,3]diazepin-3-ol hydrobromide A solution of 3 g. of bromine in 25 ml. of dichloromethane is added to a stirred solution of 5 g. of p-chlorophenyl-p-chlorobenzyl ketone in 200 ml. of dichloromethane. The mixture is allowed to stand overnight and the solvent is removed in vacuo. The residue is dissolved in 150 ml. of acetone, treated with charcoal and filtered. The filtrate represents an acetone solution of 2-(p-chlorophenyl)-2-bromo-p-chloroacetophenone and is mixed with a clarified solution of 2.5 g. of hexahydro-2H-1,3-diazepin-2-thione in 150 ml. of acetone. The mixture is allowed to stand 5 hours and then the solid is collected, washed with 100 ml. of acetone and dried in vacuo at 60° C., giving 6.7 g. of the desired product, m.p. 216°–218° C. (dec.).

EXAMPLE 6

2-(p-Chlorophenyl)-2,3,5,6,7,8-hexahydro-3-phenyl-thiazolo[3,2-a][1,3]diazepin-3-ol hydrobromide A 3 g. portion of bromine in 25 ml. of dichloromethane is added dropwise to a stirred solution of 4.3 g. of 2-p-chlorophenylacetophenone in 200 ml. of dichloromethane. The mixture is allowed to stand overnight, the solvent is removed in vacuo and the residue of 2-(p-chlorophenyl)-2-bromoacetophenone is dissolved in 150 ml. of acetone, treated with charcoal and clarified. The filtrate is mixed with a clarified solution of 2.5 g. of hexahydro-2H-1,3-diazepin-2-thione in 150 ml. of acetone and allowed to stand 5 hours. The solid is collected, washed with 100 ml. of acetone and dried in vacuo, giving 4.4 g. of the desired product, m.p. 190°–192° C. (dec.).

EXAMPLE 7

2,3,5,6,7,8-Hexahydro-2-phenyl-3-p-tolylthiazolo[3,2-a][1,3]diazepin-3-ol hydrobromide A 3 g. portion of bromine in 25 ml. of dichloromethane is added to a stirred solution of 4 g. of 2-(p-tolyl)acetophenone in 200 ml. of dichloromethane. The mixture is allowed to stand overnight, the solvent is removed in vacuo. The residue of 2-(p-tolyl)-2-bromoacetophenone is dissolved in 150 ml. of acetone, treated with charcoal, clarified and the filtrate is mixed with a clarified solution of 2.5 g. of hexahydro-2H-1,3-diazepin-2-thione in 150 ml. of acetone. This mixture is allowed to stand 6 hours, the solid is collected, washed with 100 ml. of acetone and dried in vacuo, giving 4.0 g. of the desired product, m.p. 208–210° C.

EXAMPLE 8

2,3,5,6,7,8-Hexahydro-2,3-diphenylthiazolo[3,2-a][1,3-diazepin-3-ol hydrochloride A 5.1 g. portion of 2-bromo-2-phenylacetophenone is dissolved in 100 ml. of ethanol and 2.6 g. of hexahydro-2H-1,3-diazepin-2-thione are added. The solution is refluxed for 16 hours, 4 g. of silver chloride are added and refluxing is continued for 6 hours. The mixture is clarified, cooled to −10° C., treated with charcoal and clarified. The filtrate is heated to boiling, 50 ml. of ether are added and the mixture is cooled to −10° C. and maintained at that temperature for 4 hours. The solid is collected, washed with ether and dried at 60° C. in vacuo, giving 2.2 g. of the desired product, m.p. 197°–199° C.

EXAMPLE 9

2,3,5,6,7,8-Hexahydro-3-(5-methyl-2-furyl)-2-phenyl-thiazolo[3,2-a][1,3]diazepin-3-ol hydrochloride A mixture of 10 ml. of 5-methyl-2-furfuraldehyde, 5 g. of potassium cyanide, 10.1 ml. of benzaldehyde and 100 ml. of 65% ethanol is refluxed for 2 hours and then refrigerated. The solid is collected, washed with 40% ethanol, then water and dried, and recrystallized from 125 ml. of ethanol giving 8.4 g. of (5-methyl-2-furyl)-α-hydroxybenzyl ketone.

A mixture of 2.56 ml. of methanesulfonyl chloride in 60 ml. of toluene is added to a stirred slurry of 6.48 g. of the above ketone and 8.4 g. of triethylamine in 60 ml. of toluene. The mixture is allowed to stand overnight, filtered and the yellow solid is washed with water, giving 6.4 g. of (5-methyl-2-furyl)-α-hydroxybenzyl ketone methanesulfonate.

A mixture of 2.94 g. of (5-methyl-2-furyl)-α-hydroxybenzyl ketone methanesulfonate and 1.30 g. of hexahydro-2H-1,3-diazepin-2-thione in 150 ml. of acetone is allowed to stand for 48 hours, then refrigerated, concentrated to remove the solvent and 50 ml. of water and one ml. of concentrated ammonium hydroxide are added. The solid is collected, washed with water, then dissolved in 10 ml. of ether and cooled. The mixture is filtered and the filtrate is combined with alcoholic hydrogen chloride and ether and refrigerated, giving 0.45 g. of the desired product, m.p. 193°–195° C.

EXAMPLE 10

2,3,5,6,7,8-Hexahydro-2-phenyl-3-(3,4-xylyl)-thiazolo[3,2-a][1,3]diazepin-3-ol hydrochloride A mixture of 9.4 ml. of 3,4-dimethylbenzaldehyde, 5 g. of potassium cyanide, 7.1 ml. of benzaldehyde and 100 ml. of 65% ethanol is refluxed for 2 hours, then 60 ml. of water are added and the mixture is refrigerated for two days giving an oil. The oil is slurried with toluene, washed with water, dried, concentrated and the oil is dissolved in 50 ml. of ether and refrigerated. The mixture is filtered and the filtrate is concentrated to an oil. This crude 3,4-dimethylbenzoin, in the form of an oil, is dissolved in 50 ml. of toluene and 7 ml. of triethylamine. To this solution is added, dropwise with stirring, a mixture of 2.4 ml. of methanesulfonyl chloride in 30 ml. of toluene. The mixture is allowed to stand for 20 hours, water is added, the organic layer is separated, washed with water and concentrated to an oil. This crude 3,4-dimethylbenzoin methanesulfonate is mixed with 1.30 g. of hexahydro-2H-1,3-diazepin-2-thione and 50 ml. of acetone and allowed to stand overnight. A 60 ml. portion of ether is added then the solvent is removed and 50 ml. of water and 2 ml. of ammonium hydroxide and added. Ths mixture is triturated, the water is decanted and the residue dissolved in ethanol. The solvent is concentrated almost to dryness and 5 ml. of 1.8 N alcoholic hydrogen chloride are added. The solvent is removed and the residue dissolved in 40 ml. of acetone and refrigerated. The solid is filtered, washed with ether and dried in vacuo, giving 1.7 g. of the desired product, m.p. 184°–186° C.

EXAMPLE 11

2-(p-Chlorophenyl)-2,3,5,6,7,8-hexahydro-3-[3,4-(methylenedioxy)phenyl]thiazolo[3,2-a][1,3]diazepin-3-ol hydrochloride A mixture of 14 g. of p-chlorobenzaldehyde, 15 g. of piperonal, 8 g. of potassium cyanide and 200 ml. of 50% ethanol is refluxed for 2 hours and then cooled overnight. The solid is collected, washed with water and recrystallized twice from ethanol, giving 8.8 g. of 4'-chloro-3,4-(methylenedioxybenzoin.

A mixture of 1.55 ml. of methanesulfonyl chloride and 40 ml. of toluene is added over a period of one hour to a stirred mixture of 5.8 g. of 4'-chloro-3,4-(methylenedioxy)benzoin, 5.6 ml. of triethylamine and 20 ml. of toluene. The mixture is allowed to stand 4 hours, 50 ml. of water and more toluene are added, the organic layer is separated, washed with water, dried, refrigerated and then concentrated to an oil, giving 8.3 g. of the methanesulfonate ester. This oil is dissolved in 30 ml. of acetone and added to a stirred mixture of 1.95 g. of hexahydro-2H-1,3-diazepin-2-thione in 150 ml. of acetone. The mixture is allowed to stand for 3 hours, heated at 45°–50° C. for 3 hours, refrigerated overnight and concentrated to about ⅓ its original volume. An equal volume of ether is added producing a gum. The solvent is removed, 100 ml. of water and 2 ml. of ammonium hydroxide are added. The solid is collected, washed with water, dried and dissolved in 25 ml. of ethanol. This solution is refrigerated, then filtered and to the filtrate are added alcoholic hydrogen chloride and ether. After refrigeration, the solid is filtered, washed with ether, boiled with 25 ml. of ethanol and filtered. The filtrate is treated with alcoholic hydrogen chloride and cooled, giving 0.41 g. of the desired product, m.p. 184°–186° C.

EXAMPLE 12

2-(o-Chlorophenyl)-3-(3,4-dimethoxyphenyl)-2,3,5,6,7,8-hexahydrothiazolo[3,2-a][1,3]diazepin-3-ol hydrochloride The procedure of Example 1 is repeated. After the reaction mixture is reduced to ⅓ volume and ether is added, the resulting gum is treated with alcoholic hydrogen chloride and ether and then refreigerated. The solid is collected, boiled with 25 ml. of ethanol, cooled and the solid is collected, giving 0.80 g. of the desired product, m.p. 197°–199° C.

EXAMPLE 13

2,3,5,6,7,8-Hexahydro-3-(3-methyl-2-thienyl)-2-phenylthiazolo[3,2-a][1,3]diazepin-3-ol hydrochloride A 12.6 g. portion of 3-methyl-2-thiophenecarboxaldehyde is treated as described in Example 2, giving 3-methyl-2-thienyl-α-hydroxybenzyl ketone. A mixture of 1.6 ml. of methanesulfonyl chloride and 30 ml. of toluene is added to a stirred mixture of 7.2 g. of the above ketone, 5.6 ml. of triethylamine and 50 ml. of toluene and reacted as described in Example 2, giving 3-methyl-2-thienyl-α-hydroxybenzyl ketone methanesulfonate ester as an oil. This oil is treated with 1.55 g. of hexahydro-2H-1,3-diazepin-2-thione in 50 ml. of acetone and allowed to stand overnight. A 50 ml. portion of ether is added, the solvent is removed and 50 ml. of water and 2 ml. of concentrated ammonium hydroxide are added. The aqueous layer is decanted and the residue is dissolved in ethanol and concentrated almost to dryness. A 5 ml. portion of 1.8 N alcoholic hydrogen chloride is added. The solvent is removed and the residue is dissolved in 40 ml. of acetone and refrigerated. The solid is collected, washed with ether, dried in vacuo, dissolved in 5 ml. of ethanol and refrigerated, giving 0.60 g. of the desired product, m.p. 149°–155° C.

EXAMPLE 14

3-(2,4-Dimethoxyphenyl)-2,3,5,6,7,8-hexahydro-2-phenylthiazolo[3,2-a][1,3]diazepin-3-ol hydrochloride A mixture of 11.7 g. of 2,5-dimethoxybenzaldehyde, 5 g. of potassium cyanide, 7.1 ml. of benzaldehyde and 100 ml. of 65% ethanol is refluxed for 2 hours. Water (60 ml.) is added, the organic layer is separated, washed with water and slurried with toluene. The organic layer is separated, washed with water, dried and concentrated to an oil. The crude 2,4-dimethoxybenzoin is converted to the methanesulfonate ester by the procedure of Example 1, giving an oil. This oil is combined with 1.95 g. of hexahydro-2H-1,3-diazepine-2-thione in 70 ml. of acetone and reacted as described in Example 13, giving 1.8 g. of the desired product, m.p. 202°–203° C.

EXAMPLE 15

2,3-Bis(o-chlorophenyl)-2,3,5,6,7,8-hexahydrothiazolo[3,2-a][1,3]diazepin-3-ol hydrochloride A mixture of 22.6 ml. of o-chlorobenzaldehyde, 8 g. of potassium cyanide and 100 ml. of 65% ethanol is refluxed for 2 hours and then refrigerated. Water (30 ml.) is added, refrigeration is continued, then the water layer is decanted and the oil dissolved in toluene, washed with water, dried and concentrated to an oil. The crude 2,2'-dichlorobenzoin is converted to the methanesulfonate ester as described in Example 1, giving an oil. A 14.6 g. portion of this oil is reacted with 2.6 g. of hexahydro-2H-1,3-diazepin-2-thione in 100 ml. of acetone as described in Example 13, giving 1.4 g. of the desired product, m.p. 224°–226° C.

EXAMPLE 16

2-(o-Chlorophenyl)-2,3,5,6,7,8-hexahydro-3-[3,4-(methylenedioxy)phenyl]thiazolo[3,2-a][1,3]diazepin-3-ol hydrochloride An 11.3 ml. portion of o-chlorobenzaldehyde is converted to 2'-chloro-3,4-(methylenedioxy)benzoin by the procedure of Example 11 and then converted to the methanesulfonate ester also by the procedure of Example 11. A 2.2 g. portion of this ester is reacted with 0.78 g. of hexahydro-2H-1,3-diazepin-2-thione in 70 ml. of acetone. After 48 hours the precipitate that forms is collected and dried. The yield of 2-(o-chlorophenyl)-2,3,5,6,7,8-hexahydro-3-[3,4-(methylenedioxy)phenyl]-thiazolo[3,2,-a][1,3]diazepin-3-ol methanesulfonate is 1.9 g., mp 180°–182° C. with decomposition.

If the above reaction mixture is treated with 5 ml of 2 N ethanolic hydrogen chloride, the title compound is obtained in 1.6 g. yield, m.p. 197°–199° C.

EXAMPLE 17

2-(o-Fluorophenyl)-2,3,5,6,7,8-hexahydro-3-[3,4-(methylenedioxy)phenyl]thiazolo[3,2-a][1,3]diazepin-3-ol hydrochloride A 10.5 ml. portion of o-fluorobenzaldehyde is converted to 2'-fluoro-3,4-(methylenedioxy)benzoin and then to the methanesulfonate ester by the procedure of Example 11. A 2.1 g. portion of this ester is reacted as described in Example 16, giving 1.6 g. of the desired product, m.p. 184°-186° C.

EXAMPLE 18

2-(o-Fluorophenyl)-2,3,5,6,7,8-hexahydro-3-(2-thienyl)-thiazolo[3,2-a][1,3]diazepin-3-ol hydrochloride A mixture of 9.2 ml. of 2-thiophenecarboxaldehyde, 10.5 ml. of o-fluorobenzaldehyde, 8 g. of potassium cyanide and 100 ml. of 65% ethanol is refluxed for 2 hours, refrigerated and the solid is collected, washed with 30% ethanol, water, dried and recrystallized from 50 ml. of 90% ethanol giving 7.7 g. of 2-thienyl-α-hydroxy-o-fluorobenzyl ketone. This ketone is converted to the methanesulfonate ester by the procedure of Example 1, giving 5.2 g. of pinkish crystals. A 1.88 g. portion of this ester is reacted as described in Example 16, giving 0.8 g. of the desired product, m.p. 192°-195° C.

EXAMPLE 19

2,3,5,6,7,8-Hexahydro-2,3-diphenylthiazolo[3,2-a][1,3]-diazepin-3-ol methanesulfonate A mixture of 7.75 ml. of methanesulfonyl chloride in 200 ml. of toluene is added, over a period of one hour, to a stirred mixture of 21.2 g. of benzoin, 28 ml. of triethylamine and 100 ml. of toluene. The mixture is allowed to stand 2 hours, 100 ml. of water is added and the emulsion is filtered giving a solid which is washed with water and dried, giving 14.5 g. of benzoin methanesulfonate esters. A 2.90 g. portion of benzoin methanesulfonate esters and 1.30 g. of hexahydro-2H-1,3-diazepin-2-thione are suspended in 50 ml. of warm acetone and heated at reflux for 4 hours. The mixture is cooled, the solid is collected, washed with acetone then ether and dried in vacuo at 60° C., giving 3.9 g. of the desired product, m.p. 176°-178° C.

EXAMPLE 20

2-(o-Chlorophenyl)-3-(p-dimethylaminophenyl)-2,3,5,6,7,8-hexahydrothiazolo[3,2-a][1,3]diazepin-3-ol methanesulfonate A mixture of 15 g. of p-dimethylaminobenzaldehyde, 15 g. of o-chlorobenzaldehyde, 4 g. of potassium cyanide and 90 ml. of 65% ethanol is refluxed for one hour, ice water is added and the mixture is refrigerated for 48 hours. The solid is collected, washed with water, dried and boiled with 200 ml. of ethanol, giving 8.8 g. of 2'-chloro-4-dimethylaminobenzoin.

A 1.55 ml. portion or methanesulfonyl chloride in 40 ml. of toluene is added over a one hour period to a stirred mixture of 5.79 g. of 2'-chloro-4-dimethylaminobenzoin and 5.6 ml. of triethylamine in 20 ml. of toluene. The mixture is allowed to stand 4 hours, 50 ml. of water and more toluene are added and the solid is collected, giving 6.4 g. of 2'-chloro-4-dimethylaminobenzoin methanesulfonate ester.

A mixture of 2.76 g. of this ester and 0.91 g. of hexahydro-2H-1,3-diazepin-2-thione in 40 ml. of acetone is heated at reflux for 2 hours, clarified and refrigerated. Ether is added and the mixture is further refrigerated. The solvent layer is decanted and the residual oil is triturated with acetone giving a solid which is collected and washed with ether. The yield of the desired product is 1.0 g, m.p. 176°-178° C.

EXAMPLE 21

2-(o-Chlorophenyl)-2,3,5,6,7,8-hexahydro-3-(p-methoxyphenyl)thiazolo[3,2-a][1,3]diazepin-3-ol methanesulfonate A 14.0 g. portion of o-chlorobenzaldehyde, 13.6 g. of p-anisaldehyde, 8 g. of potassium cyanide and 150 ml. of 50% ethanol are reacted as described in Example 20, giving 13.8 g. of 2'-chloro-4-methoxybenzoin. A 5.5 g. portion of this compound is then converted to the methanesulfonate ester by the procedure of Example 20, giving 7.8 g. as an oil. This oil is dissolved in 30 ml. of acetone and added to a stirred mixture of 1.95 g. of hexahydro-2H-1,3-diazepin-2-thione. The mixture is stirred overnight, the solid is collected, washed with ether and dried in vacuo, giving 2.5 g. of the desired product, m.p. 186°-188° C.

EXAMPLE 22

2-(m-Chlorophenyl)-3-(p-dimethylaminophenyl)-2,3,5,6,7,8-hexahydrothiazolo[3,2-a][1,3]diazepin-3-ol methanesulfonate A mixture of 11.2 g. of p-dimethylaminobenzaldehyde, 10.5 g. of m-chlorobenzaldehyde, 6.0 g. of potassium cyanide and 130 ml. of 50% ethanol is refluxed for 2 hours, cooled and the solid is collected, washed with water, boiled with 110 ml. of methanol, clarified and cooled giving 6.6 g. of 3'-chloro-4-dimethylaminobenzoin, 4.35 g. of which is converted to the methanesulfonate ester by the procedure of Example 20, giving 4.2 g. A 3.68 g. portion of this ester and 1.17 g. of hexahydro-2H-1,3-diazepine-2-thione in 130 ml. of acetone is stirred for 48 hours and the solid is collected, washed with ether and dried, giving 2.9 g. of the desired product, m.p. 176°-178° C.

EXAMPLE 23

2-(m-Bromophenyl)-3-(p-dimethylaminophenyl)-2,3,5,6,7,8-hexahydrothiazolo[3,2-a][1,3]diazepin-3-ol methanesulfonate A mixture of 11.2 g. of p-dimethylaminobenzaldehyde, 13.5 g. of m-bromobenzaldehyde, 4.5 g. of potassium cyanide and 70 ml. of 65% ethanol is reacted as described in Example 20, giving 6.4 g. of 3'-bromo-4-dimethylaminobenzoin which is converted to the methanesulfonate ester by the procedure of Example 20, giving 4.4 g. A 3.3 g. portion of this ester and 0.97 g. of hexahydro-2H-1,3-diazepin-2-thione in 130 ml. of acetone are stirred for 48 hours and the solid is collected, washed with ether and dried in vacuo giving 2.4 g. of the desired product, m.p. 173°-175° C.

EXAMPLE 24

2,3,5,6,7,8-Hexahydro-3-(p-methoxyphenyl)-2-phenyl-thiazolo[3,2-a][1,3]diazepin-3-ol methanesulfonate A mixture of 13.6 g. (12.2 ml.) of anisaldehyde, 10.6 g. of benzaldehyde, 3 g. of potassium cyanide and 50 ml. of 95% ethanol is reacted as described in Example 20, giving 6.1 g. of 4-methoxybenzoin. A 4.85 g. portion of this compound is converted to the methanesulfonate ester by the procedure of Example 20, giving 5.0 g. of ester. A mixture of 3.20 g. of this ester, 1.30 g. of hexahydro-2H-1,3-diazepin-2-thione and 100 ml. of acetone is allowed to stand for 48 hours, then the solid is collected, washed with ether and dried in vacuo, giving 3.2 g. of the desired product, m.p. 152°-153° C.

EXAMPLE 25

2,3,5,6,7,8-Hexahydro-2-phenyl-3-(2-thienyl)thiazolo-[3,2-a][1,3]diazepin-3-ol methanesulfonate A mixture of 9.2 ml. of thiophene-2-carboxyaldehyde, 8 g. of potassium cyanide and 10.1 ml. of benzaldehyde in 100 ml. of 65% ethanol is reacted as described in Example 20, giving 6.2 g. of 2-thienyl-α-hydroxybenzyl ketone. A 4.36 g. portion of this ketone is reacted with methanesulfonyl chloride as described in Example 20, giving 3.2 g. of the methanesulfonate ester. A 2.64 g. portion of this ester and 1.30 g. of hexahydro-2H-1,3-diazepine-2-thione in 100 ml. of acetone are allowed to stand 48 hours, the solid is collected, washed with ether and dried in vacuo, giving 2.8 g. of the desired product, m.p. 149°-151° C.

EXAMPLE 26

3-(2-Furyl)-2,3,5,6,7,8-hexahydro-2-phenylthiazolo-[3,2-a][1,3]diazepin-3-ol methansulfonate A mixture of 10.6 g. (10.1 ml.) of benzaldehyde, 9.6 g. (8.3 ml.) of 2-furaldehyde, 5 g. of potassium cyanide and 100 ml. of 65% ethanol is reacted as described in Example 20, giving 2.7 g. of 2-furyl-α-hydroxybenzyl ketone, a 2.42 g. portion of which is converted to the methanesulfonate ester as described in Example 20, giving 2.2 g. of ester. A 1.7 g. portion of this ester and 0.78 g. of hexahydro-2H-1,3-diazepin-2-thione in 90 ml. of acetone are stirred for 48 hours, the solid is collected, washed with ether and dried in vacuo, giving 2.0 g. of the desired product, m.p. 172°-174° C.

EXAMPLE 27

2,3,5,6,7,8-Hexahydro-3-[3,4-(methylenedioxy)phenyl]-2-phenylthiazolo[3,2-a][1,3]diazepin-3-ol methanesulfonate A mixture of 15 g. of piperonal, 10.6 g. (10.1 ml.) of benzaldehyde, 5 g. of potassium cyanide and 150 ml. of 50% ethanol is reacted as described in Example 20, giving 3.3 g. of 3,4-(methylenedioxy)benzoin. A 2.82 g. portion of this compound is converted to the methanesulfonate ester by the procedure of Example 20, giving 2.1 g. of the ester. A mixture of 1.67 g. of this ester, 0.65 g. of hexahydro-2H-1,3-diazepin-2-thione and 30 ml. of acetone is allowed to stand 48 hours, the solid is collected, washed with ether and dried in vacuo, giving 2.2 g. of the desired product, m.p. 176°-178° C.

EXAMPLE 28

2-(o-Chlorophenyl)-2,3,5,6,7,8-hexahydro-3-[3,4-(methylenedioxy)phenyl]thiazolo[3,2-a][1,3]diazepin-3-ol methanesulfonate A 2.1 g. portion of 2'-chloro-3,4-(methylenedioxy)-benzoin methanesulfonate ester, prepared as described in Example 16, is dissolved in 20 ml. of acetone and a solution of 0.78 g. of hexahydro-2H-1,3-diazepin-2-thione in 50 ml. of acetone is added. The mixture is allowed to stand 48 hours and the solid is collected, giving 1.9 g. of the desired product, m.p. 180°-182° C.

EXAMPLE 29

2,3,5,6,7,8-Hexahydro-2,3-diphenylthiazolo[3,2-a][1,3]-diazepin-3-ol L-tartrate

A solution of 3.42 g. of 2,3,5,6,7,8-hexahydro-2,3-diphenylthiazolo[3,2-a][1,3]diazepin-3-ol, prepared as described in Example 4, in acetone is treated with a solution of 1.50 g. of L-tartaric acid in acetone. Isopropanol is added and the mixture is warmed briefly to dissolve the gum which forms. After cooling, the solid is collected and recrystallized from a mixture of methanol and isopropanol, giving 3.15 g. of the desired product, m.p. 138°-140° C.

EXAMPLE 30

2-(p-Chlorophenyl)-2,3,5,6,7,8-hexahydro-3-[3,4-(methylenedioxy)phenyl]thiazolo[3,2-a][1,3]diazepin-3-ol An 8.3 g. portion of 4'-chloro-3,4-(methylenedioxy)-benzoin methanesulfonate ester, prepared as described in Example 11, in 30 ml. of acetone is added to a stirred mixture of 1.95 g. of hexahydro-2H-1,3-diazepin-2-thione in 150 ml. of acetone. The mixture is allowed to stand 3 hours and heated at 45°-50° C. for 3 hours. The mixture is concentrated to remove the solvent and 100 ml. of water and 2 ml. of ammonium hydroxide are added. The solid is collected, dissolved in 25 ml. of ethanol and refrigerated, giving 1.8 g. of the desired product, m.p. 105°-107° C.

EXAMPLE 31

2-(o-Chlorophenyl)-2,3,5,6,7,8-hexahydro-3-(2-thienyl)-thiazolo[3,2-a][1,3]diazepin-3-ol A mixture of 9.2 ml. of 2-thiophenecarboxaldehyde, 11.3 ml. of o-chlorobenzaldehyde, 8 g. of potassium cyanide and 100 ml. of 65% ethanol is refluxed for 2 hours and then refrigerated. A 30 ml. portion of water is added, refrigeration is continued, the oil is separated by decantation, added to toluene, washed with water, dried and concentrated giving 12.7 g. of an oil. A 9.0 g. portion of this oil is mixed with 8.4 ml. of triethylamine and 100 ml. of toluene and stirred as a mixture of 2.4 ml. of methanesulfonyl chloride in 100 ml. of toluene is added. The mixture is stirred overnight then 100 ml. of water is added. The toluene layer is separated, washed with water, dried and concentrated, giving 10.6 g. of oily 2-thienyl α-hydroxy(2-chlorophenyl)ketone. This oil is combined with 3.9 g. of hexahydro-2H-1,3-diazepin-2-thione in 150 ml. of acetone and allowed to stand 48 hours. The solvent is removed, 100 ml. of water and 2 ml. of ammonium hydroxide are added and the aqueous layer is decanted. Ethanol is added, the mixture is cooled and the solid is collected, giving 3.4 g. of the desired product, m.p. 120°-122° C.

EXAMPLE 32

3-(2,6-Dichlorophenyl)-2,3,5,6,7,8-hexahydro-2-phenylthiazolo[3,2-a][1,3]diazepin-3-ol hydrobromide A 3 g. portion of bromine in 25 ml. of dichloromethane is added to a stirred mixture of 5 g. of 2-(2,6-dichlorophenyl)acetophenone in 200 ml. of dichloromethane. The mixture is stored overnight, the solvent is removed in vacuo, the residue of 2-bromo-2-(2,6-dichlorophenyl)acetophenone is dissolved in 150 ml. of acetone, treated with charcoal, clarified and the filtrate mixed with a clarified solution of 2.5 g. of hexahydro-2H-1,3-diazepin-2-thione in 150 ml. of acetone. The mixture is allowed to stand overnight, taken to dryness in vacuo and the residue is boiled in 200 ml. of ether giving 3.0 g. of the desired product.

EXAMPLE 33

2,3-Diphenyl-2,3,5,6,7,8-hexahydrothiazolo[3,2-a][1,3]diazepin-3-ol salt with [2,3-Dichloro-4-(2'-thienylcarbonyl)]phenoxyacetic acid Three grams of 2,3,5,6,7,8-hexahydro-2,3-diphenyl-thiazolo[3,2-a][1,3]diazepin-3-ol (Example 4) are dissolved in 100 ml of acetone and added to a solution of three grams of [2,3-dichloro-4-(2'-thienylcarbonyl)]-phenoxyacetic acid in 100 ml of acetone. The resultant solution slowly deposits a crystalline precipitate. After three days, the precipitate is collected and dried, yield, 4.0 grams, melting point 161°–162° with decomposition.

EXAMPLE 34

3-(p-Dimethylaminophenyl)-2-(o-fluorophenyl)-2,3,5,6,7,8-hexahydrothiazolo[3,2-a][1,3]diazepin-3-ol methanesulfonate A mixture consisting of 14.9 g. of p-dimethylaminobenzaldehyde, 12.4 g. of o-fluorobenzaldehyde, 8 g. of potassium cyanide, and 100 ml. of 65% ethanol is reacted as described in Example 20, giving 12.6 g. of 4'-dimethylamino-2'-fluorobenzoin, m.p. 150°–155° C. A 5.47 g. portion of this compound is converted to the methanesulfonate ester by the procedure of Example 20, giving 5.1 g. of ester melting at 136°–138° C. A mixture of 1.92 g. of the methanesulfonate ester, 0.65 g. of hexahydro-2H-1,3-diazepin-2-thione, and 60 ml. of acetone is left at room temperature for two days, yielding 1.5 g. of the title compound, m.p. 172°–179° C.

EXAMPLE 35

2-(m-Fluorophenyl)-2,3,5,6,7,8-hexahydro-3-(3,4-methylenedioxyphenyl)thiazolo[3,2-a][1,3]diazepin-3-ol hydrochloride A mixture consisting of 12 g. of piperonal, 10 g. of m-fluorobenzaldehyde, 6 g. of potassium cyanide, and 80 ml. of 65% ethanol is reacted as described in Example 20, giving 4.7 g. of 3'-fluoro-3',4'-methylenedioxybenzoin, m.p. 99°–101° C. A 4.4 g. portion of this benzoin is converted to the methanesulfonate ester by the procedure of Example 20, 4.2 g. of the ester being obtained, m.p. 117°–120° C. A 1.76 g. portion of this ester, 0.75 g. of hexahydro-2H-1,3-diazepin-2-thione, and 40 ml. of acetone is left at room temperature for two days. 5 ml. of 2 N ethanolic hydrogen chloride is added, giving the title compound in 1.3 g. yield, m.p. 192°–194° C.

EXAMPLE 36

2-(o-Fluorophenyl)-2,3,5,6,7,8-hexahydro-3-(p-methoxyphenyl)thiazolo[3,2-a][1,3-a]diazepin-3-ol hydrochloride A mixture consisting of 13.6 g. of p-anisaldehyde, 12.4 g. of o-fluorobenzaldehyde, 8 g. of potassium cyanide, and 100 ml of 65% ethanol is reacted as described in Example 20, yielding 6.7 g. of 2'-fluoro-4'-methoxybenzoin, m.p. 65°–67° C. A 5.2 g. portion of the benzoin derivative is converted to its methanesulfonate ester by the procedure of Example 20, yielding 7.9 g. of ester as an oil. 3.4 grams of the crude methanesulfonate ester, 1.04 g. of hexahydro-2H-1,3-diazepin-2-thione, and 70 ml of acetone are combined and left at room temperature for two days. 6 ml. of 2 N ethanolic hydrogen chloride are added to the solution, precipitating 2.1 g. of the title compound melting at 192°–194° C.

EXAMPLE 37

3-(3,4-Dimethoxyphenyl)-2-(o-fluorophenyl)-2,3,5,6,7,8-hexahydrothiazolo[3,2-a][1,3]diazepin-3-ol hydrochloride A mixture consisting of 16.6 g. of veratraldehyde, 12.5 g. of o-fluorobenzaldehyde, 8 g. of potassium cyanide, and 100 ml of 65% ethanol is reacted as described in Example 20, yielding 12.5 g. of 3,4-dimethoxy-2'-fluorobenzoin, m.p. 126°–128° C. A 5.8 g. portion of the benzoin derivative is converted to its methanesulfonate ester by the procedure of Example 20, giving 6.7 g. of the ester melting at 111°–113° C. 2.58 g. of the methanesulfonate ester, 0.91 g. of hexahydro-2H-1,3-diazepin-2-thione, and 55 ml. of acetone are mixed and left at room temperature for three days. 7 ml. of 2 N ethanolic hydrogen chloride are added, yielding 2.2 g. of the title compound, melting at 192°–194° C.

EXAMPLE 38

2-(p-Fluorophenyl)-3-(3,4-methylenedioxyphenyl)-2,3,5,6,7,8-hexahydrothiazolo[3,2-a][1,3]diazepin-3-ol hydrochloride A mixture consisting of 12 g. of piperonal 8.4 ml. of p-fluorobenzaldehyde, 6 g. of potassium cyanide, and 80 ml. of 65% ethanol is reacted as described in Example 20, giving 11.7 g. of 4'-fluoro-3,4-methylenedioxybenzoin as an uncrystallizable oil. 9.0 g. of this benzoin is converted to its methanesulfonate ester by the procedure of Example 20, yielding 9.8 g. of ester as an uncrystallizable oil. The reaction of 4.9 g. of the crude methanesulfonate ester, and 1.16 g. of hexahydro-2H-1,3-diazepin-2-thione in 80 ml. of acetone, followed by treatment with 5 ml of 2 N ethanolic hydrogen chloride gives the title compound melting at 211°–213° C.

EXAMPLE 39

3-(3,4-Dimethoxyphenyl)-2-(m-fluorophenyl)-2,3,5,6,7,8-hexahydrothiazolo[3,2-a][1,3]diazepin-3-ol hydrochloride A mixture consisting of 13.2 g. of veratraldehyde, 10 g. of m-fluorobenzaldehyde, 6 g. of potassium cyanide, and 8 ml. 65% ethanol are reacted according to the procedure of Example 20, yielding 3.6 g. of 3,4-dimethoxy-3'-fluorobenzoin as a viscous oil. The benzoin is converted to its methanesulfonate ester by the procedure of Example 20, giving the ester in 4.2 g. yield as an uncrystallizable oil. 2.1 g. of the methanesulfonate ester, 0.52 g. of hexahydro-2H-1,3-diazepin-2-thione, and 40 ml. of acetone are combined and left at room temperature for three days. Addition of 5 ml. of 2 N ethanolic hydrogen chloride gives 0.42 g. of the title compound, m.p. 194°–196° C.

EXAMPLE 40

3-(p-Dimethylaminophenyl)-2,3,5,6,7,8-hexahydro-2-phenylthiazolo[3,4-a][1,3]diazepin-3-ol methanesulfonate A mixture consisting of 9.5 g. of p-dimethylaminobenzaldehyde, 6.06 ml. of benzaldehyde, 4 g. of 4'-dimethylaminobenzoin, m.p. 161°–163° C. 1.83 g. of the methanesulfonate ester, 0.71 g. of hexahydro-1H-1,3-diazepin-2-thione, and 50 ml. of acetone are combined and left at room temperature for three days. No precipitate is noted, so ether is added to the turbidity point, and the mixture left at room temperature overnight. The precipitate present is collected, washed with ether, and dried, giving 1.9 g. of the title compound, m.p. 181°–183° C.

EXAMPLE 41

3-(p-Dimethylaminophenyl)-2-(m-fluorophenyl)-2,3,5,6,7,8-hexahydrothiazolo[3,2-a][1,3]diazepin-3-ol methanesulfonate A mixture consisting of 14.9 g. of p-dimethylaminobenzaldehyde, 12.4 g. of m-fluorobenzaldehyde, 6 g. of potassium cyanide, and 100 ml. of 65% ethanol is reacted according to the procedure of Example 20, 12.8 g. of 4-dimethylamino-3'-fluorobenzoin being obtained; m.p. 147°–149° C. An 8.2 g. portion of this benzoin is converted to its methanesulfonate ester, by the procedure of Example 20, in 9.1 g. yield, m.p. 106°–109° C. A mixture of 2.6 g. of the methanesulfonate ester, 0.91 g. of hexahydro-2H-1,3-diazepin-2-thione, and 70 ml. of acetone is left at room temperature for three days, precipitating the title compound in 2.7 g. yield, m.p. 180°–182° C.

EXAMPLE 42

2-(m-Fluorophenyl)-3-(2-furyl)-2,3,5,6,7,8-hexahydrothiazolo[3,2-a][1,3]diazepin-3-ol methanesulfonate A mixture consisting of 8.3 ml. of furfuraldehyde, 12.4 g. of m-fluorobenzaldehyde, 6 g. of potassium cyanide and 100 ml. of 65% ethanol is reacted according to the procedure of Example 20, yielding 7.0 g. of 2-furyl-α-hydroxy-m-fluorobenzyl ketone, m.p. 111°–112° C. 8.4 g. of 2-furyl α-hydroxy-m-fluorobenzyl ketone is converted to its methanesulfonate ester by the procedure of Example 20 in 8.4 g. yield, m.p. 140°–154° C. 2.08 g. of the methanesulfonate ester, 0.91 g. of tetrahydro-2H-1,3-diazepin-2-thione, and 70 ml. acetone are mixed and left at room temperature for three days giving 2.0 g. of the subject compound melting at 165°–167° C.

EXAMPLE 43

3-(p-Dimethylaminophenyl)-2-(p-fluorophenyl)-2,3,5,6,7,8-hexahydrothiazolo[3,2-a][1,3]diazepin-3-ol methanesulfonate A mixture consisting of p-dimethylaminobenzaldehyde, 12.4 g. of p-fluorobenzaldehyde, 6 g. of potassium cyanide, and 100 ml. of 65% ethanol is reacted according to the procedure of Example 20 to yield 3.9 g. of 4-dimethylamino-4'-fluorobenzoin, m.p. 144°–146° C. 7.6 g. of the benzoin is converted to its methanesulfonate ester by the procedure of Example 20 in 7.2 g. yield, m.p. 138°–140° C. A mixture of 1.75 g. of the methanesulfonate ester, 0.65 g. of tetrahydro-1,3-diazepin-2-thione, and 50 ml. of acetone is left at room temperature for three days, yielding 2.0 g. of the subject compound, m.p. 172°–174° C.

We claim:

1. A compound selected from the group consisting of those of the formula:

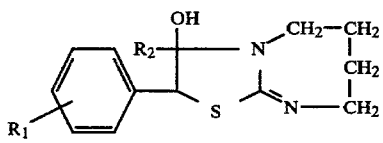

wherein $R_1$ is hydrogen, fluoro, chloro or bromo and $R_2$ is 3,4-methylenedioxyphenyl, 2-furyl, 3-methyl-2-furyl, 5-methyl-2-furyl, 2-thienyl, 3-methyl-2-thienyl, 5-methyl-2-thienyl or a moiety of the formula:

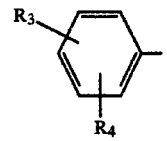

wherein $R_3$ and $R_4$ are each individually selected from the group consisting of hydrogen, fluoro, chloro, bromo, alkyl having from 1 to 3 carbon atoms, alkoxy having from 1 to 3 carbon atoms and dimethylamino; and the pharmacologically acceptable acid-addition salts thereof.

2. The compound according to claim 1; 2,3-diphenyl-2,3,5,6,7,8-hexahydrothiazolo[3,2-a][1,3]diazepin-3-ol.

3. The compound according to claim 1; 2,3-diphenyl-2,3,5,6,7,8-hexahydrothiazolo[3,2-a][1,3]diazepin-3-ol hydrochloride.

4. The compound according to claim 1; 2,3-diphenyl-2,3,5,6,7,8-hexahydrothiazolo[3,2-a][1,3]diazepin-3-ol hydrobromide.

5. The compound according to claim 1; 2,3-diphenyl-2,3,5,6,7,8-hexahydrothiazolo[3,2-a][1,3]diazepin-3-ol L-tartrate.

6. The compound according to claim 1; 2,3-diphenyl-2,3,5,6,7,8-hexahydrothiazolo[3,2-a][1,3]diazepin-3-ol methanesulfonate.

7. The compound according to claim 1; 2-(p-chlorophenyl)-3-phenyl-2,3,5,6,7,8-hexahydrothiazolo[3,2-a][1,3]diazepin-3-ol hydrobromide.

8. The compound according to claim 1; 2-phenyl-3-(3,4-xylyl)-2,3,5,6,7,8-hexahydrothiazolo[3,2-a][1,3]diazepin-3-ol hydrochloride.

9. The compound according to claim 1; 2-phenyl-3-(2,4-dimethoxyphenyl)-2,3,5,6,7,8-hexahydrothiazolo[3,2-a]-[1,3]diazepin-3-ol hydrochloride.

10. The compound according to claim 1; 2-phenyl-3-(p-methoxyphenyl)-2,3,5,6,7,8-hexahydrothiazolo[3,2-a][1,3]diazepin-3-ol methanesulfonate.

11. The compound according to claim 1; 2-(m-bromophenyl)-3-(p-dimethylaminophenyl)-2,3,5,6,7,8-hexahydrothiazolo[3,2-a][1,3]diazepin-3-ol methanesulfonate.

12. The compound according to claim 1; 2-phenyl-3-(2-furyl)-2,3,5,6,7,8-hexahydrothiazolo[3,2-a][1,3]diazepin-3-ol methanesulfonate.

13. The compound according to claim 1; 2-phenyl-3-(3,4-methylenedioxyphenyl)-2,3,5,6,7,8-hexahydrothiazolo[3,2-a][1,3]diazepin-3-ol methanesulfonate.

14. The compound according to claim 1; 2-(p-chlorophenyl)-3-(3,4-methylenedioxyphenyl)-2,3,5,6,7,8-hexahydrothiazolo[3,2-a][1,3]diazepin-3-ol.

15. The compound according to claim 1; 2-(o-fluorophenyl)-3-(p-dimethylaminophenyl)-2,3,5,6,7,8-hexahydrothiazolo[3,2-a][1,3diazepin-3-ol methanesulfonate.

16. The compound according to claim 1; 2-(o-chlorophenyl)-3-(3,4-dimethoxyphenyl)-2,3,5,6,7,8-hexahydrothiazolo[3,2-a][1,3]diazepin-3-ol hydrochloride.

17. A pharmaceutical composition for inducing diuresis in oral dosage unit form comprising from about one to about 100 mg. of a compound according to claim 1 in association with a pharmaceutical carrier.

18. The method of inducing diuresis in a mammal which comprises administering orally to said mammal an effective amount of a compound according to claim 1.

* * * * *